United States Patent [19]
Bank et al.

[11] Patent Number: 5,424,470
[45] Date of Patent: Jun. 13, 1995

[54] UNSATURATED KETONES AS ACCELERATORS FOR HYDROSILATION

[75] Inventors: Howard M. Bank, Freeland; Gary T. Decker, Midland, both of Mich.

[73] Assignee: Dow Corning Corporation, Midland, Mich.

[21] Appl. No.: 329,819

[22] Filed: Oct. 27, 1994

[51] Int. Cl.$^6$ .............................................. C07F 7/08
[52] U.S. Cl. ................................................... 556/479
[58] Field of Search ........................................ 556/479

[56] References Cited

U.S. PATENT DOCUMENTS

| | | | |
|---|---|---|---|
| 2,823,218 | 2/1958 | Speier et al. | 260/448.2 |
| 3,220,972 | 11/1965 | Lamereaux | 269/46.5 |
| 4,578,497 | 3/1986 | Onopchenko et al. | 556/479 |
| 5,359,111 | 10/1994 | Kleyer et al. | 556/479 |
| 5,359,113 | 10/1994 | Bank | 556/479 |

Primary Examiner—Paul F. Shaver
Attorney, Agent, or Firm—William F. Boley

[57] ABSTRACT

A hydrosilation process where a silicon hydride is reacted with an unsaturated reactant in the presence of a platinum catalyst and an unsaturated ketone accelerator. The described unsaturated ketone accelerators are especially useful for the hydrosilation of unsaturated reactants where the unsaturation is in the internal portion of the reactant's structure, for example, as in cyclopentene and cyclohexene. The unsaturated ketone accelerators are effective in the absence of oxygen activation of the platinum catalyst and are synergetic with oxygen activation of platinum catalyst.

18 Claims, No Drawings

UNSATURATED KETONES AS ACCELERATORS FOR HYDROSILATION

BACKGROUND OF INVENTION

The present invention is a hydrosilation process where a silicon hydride is reacted with an unsaturated reactant in the presence of a platinum catalyst and an unsaturated ketone accelerator. The unsaturated ketone accelerators are especially useful for the hydrosilation of unsaturated reactants where the unsaturation is in the internal portion of the compound's structure, for example, as in cyclopentene and cyclohexene. The unsaturated ketone accelerators are effective in the absence of oxygen activation of the platinum catalyst and are synergetic with oxygen activation of platinum catalyst.

It is known in the art to produce organosilicon compounds by reacting a silicon hydride containing compound with an unsaturated organic compound in the presence of a catalyst. This reaction is typically referred to as hydrosilation or hydrosilylation. Typically the catalyst is platinum metal on a support, a platinum compound generally in a solvent, or a platinum complex.

In Speier et al., U.S. Pat. No. 2,823,218, a method for the production of organosilicon compounds by reacting an Si-H with a compound containing aliphatic carbon atoms linked by multiple bonds in the presence of chloroplatinic acid is taught. Lamoreaux, U.S. Pat. No. 3,220,972, teaches a similar process, however the catalyst is a reaction product of chloroplatinic acid.

One of the major problems known in the art with hydrosilation reactions is the de-activation of the catalyst prior to the completion of the reaction. One method for reactivation of the catalyst has been to expose the reaction mixture to oxygen. For example, Onopchenko et al., U.S. Pat. No. 4,578,497, teaches the use of an oxygenated platinum containing catalyst for use in hydrosilating alkylsilanes. Kleyer et al., EP Patent Application No. 0533170A1, discloses a method for controlling hydrosilation reaction mixtures by controlling the solution concentration of oxygen in the reaction mixture, relative to the platinum present in the reaction mixture.

In addition to the problem of de-activation of the platinum catalyst, hydrosilation processes taught in the art are not particularly effective in hydrosilating internal unsaturated bonds in organic molecules. The present inventors have unexpectly discovered that unsaturated ketones can act as accelerators for platinum catalyzed hydrosilation processes. The unsaturated ketone accelerators can improve yield of the process in the presence or absence of oxygen and are particularly effective in facilitating the hydrosilation of internal unsaturated bonds of organic molecules.

SUMMARY OF INVENTION

The present invention is a hydrosilation process where a silicon hydride is reacted with an unsaturated reactant in the presence of a platinum catalyst and an unsaturated ketone accelerator. The unsaturated ketone accelerators are especially useful for the hydrosilation of unsaturated reactants where the unsaturation is in the internal portion of the compound's structure, for example, as in cyclopentene and cyclohexene. The unsaturated ketone accelerators are effective in the absence of oxygen activation of the platinum catalyst and are synergetic with oxygen activation of platinum catalyst.

DESCRIPTION OF INVENTION

The present invention is a hydrosilation process where a silicon hydride is reacted with an unsaturated reactant in the presence of a platinum catalyst and an unsaturated ketone accelerator. The hydrosilation process comprises: contacting
(A) a silicon hydride described by formula

  (1)

$$R^1_a H_b SiCl_{4-a-b}$$

where each $R^1$ is independently selected from a group consisting of alkyls comprising one to 12 carbon atoms, cycloalkyls comprising four to 12 carbon atoms, and aryls; a=0 to 3, b=1 to 3, and a+b=1 to 4; and
(B) an unsaturated reactant selected from a group consisting of
  (i) substituted and unsubstituted unsaturated organic compounds,
  (ii) silicon compounds comprising substituted or unsubstituted unsaturated organic substituents, and
  (iii) mixtures of (i) and (ii);
in the presence of a catalyst selected from a group consisting of platinum compounds and platinum complexes, and an accelerator selected from a group consisting of unsaturated ketones described by formulas

  (2)

$$R^2CO(CH_2)_n CH=CR^3 R^4 \text{ and}$$

  (3)

$$\overline{COCH=CR^3(CR^3_2)_m}\,;$$

where $R^2$ is selected from a group consisting of alkyls comprising one to 12 carbon atoms, each $R^3$ is independently selected from a group consisting of hydrogen and alkyls comprising one to four carbon atoms, $R^4$ is selected from a group consisting of hydrogen and non-aryl monovalent hydrocarbon radicals comprising about one to 12 carbon atoms, n=0 to 4, and m=1 to 17.

The contacting of the silicon hydride with the unsaturated reactant can be effected in standard type reactors for conducting hydrosilation processes. The contact and reaction may be run as a continuous, semi-continuous, or batch reaction.

Silicon hydrides which are useful in the present process are described by formula (1), where each $R^1$ is independently selected from a group consisting of alkyls comprising one to 12 carbon atoms, cycloalkyls comprising four to 12 carbon atoms, and aryls; a=0 to 3, b=1 to 3, and a+b=1 to 4. $R^1$ can be a substituted or unsubstituted alkyl, cycloalkyl, or aryl as described.

In formula (1) it is preferred that each $R^1$ be independently selected from a group consisting of alkyls comprising about one to six carbon atoms. Even more preferred is when each $R^1$ is methyl. Examples, of silicon hydrides described by formula (1) which may be useful in the present process include trimethylsilane, dimethylsilane, triethylsilane, dichlorosilane, trichlorosilane, methyldichlorosilane, dimethylchlorosilane, ethyldichlorosilane, cyclopentyldichlorosilane, methylphenylchlorosilane, and (3,3,3-trifluoropropyl)dichlorosilane. Examples of preferred silicon hydrides described by formula (1) include methyldichlorosilane and dichlorosilane.

The silicon hydride is contacted with an unsaturated reactant selected from a group consisting of (i) substituted and unsubstituted unsaturated organic compounds, (ii) silicon compounds comprising substituted and unsubstituted unsaturated organic substituents, and (iii) mixtures of (i) and (ii). For purpose of this invention, "unsaturated" means that the compound contains at least one carbon-carbon double bond.

More specific examples of the unsaturated reactants useful in the present process include unsubstituted cycloalkene compounds comprising at least four carbon atoms, substituted cycloalkene compounds comprising at least 4 carbon atoms, linear alkene compounds comprising about two to 30 carbon atoms, branched alkene compounds comprising four to about 30 carbon atoms, and mixtures of two or more of any of the above.

The substituted and unsubstituted cycloalkene compounds useful in the present process are those containing one or more unsaturated carbon-carbon bonds in the ring. The unsubstituted cycloalkene compounds may be, for example, cyclobutene, cyclopentene, cyclohexene, cycloheptene, cyclooctene, cyclopentadiene, 1,3-cyclohexadiene, and 1,3,5-cycloheptatriene. Substituted unsaturated compounds useful in the present invention may be, for example, 3-methylcyclopentene, 3-chlorocyclobutene, 4-phenylcyclohexene, and 3-methylcyclopentadiene. The preferred cycloalkene compounds are cyclohexene and cyclopentene, with cyclohexene being the most preferred.

Other unsaturated organic compounds useful in the present process are linear and branched alkenyl compounds including, for example, compounds with terminal unsaturation such as 1-hexene and 1,5-hexadiene, compounds with internal unsaturation such as trans-2-hexene, and unsaturated aryl containing compounds such as styrene and α-methylstyrene.

The unsaturated reactants may also comprise halogen, oxygen in the form of acids, anhydrides, alcohols, esters, and ethers; and nitrogen. Two or more of the above described unsaturated organic compounds may be used in the present process.

The unsaturated organic compounds comprising halogen may include, for example, vinyl chloride, allyl chloride, allyl bromide, allyl iodide, allyl bromide, methallyl chloride, trichloroethylene, tetrachloroethylene, tetrafluoroethylene, chloroprene, vinylidene chloride, and dichlorostyrene.

Suitable unsaturated organic compounds comprising oxygen can include, for example, ethers such as allyl and vinyl ethers; alcohols such as allyl alcohol (vinyl carbinol), methylvinylcarbinol and ethynyldimethylcarbinol; acids such as acrylic, methacrylic, vinylacetic, oleic, sorbic, and linolenic; and esters such as vinyl acetate, allyl acetate, butenyl acetate, allyl stearate, methylacrylate, ethylcrotonate, dially succinate and dially phthalate. Suitable nitrogen containing unsaturated organic compounds include, for example, indigo, indole, acrylonitrile, and allyl cyanide.

Specifically included within the definition of unsaturated organic compounds are those substituted by organofunctional moieties such as

$CH_2=CHCH_2OC(O)C(CH_3)=CH_2$,

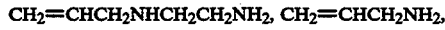
$CH_2=CHCH_2NHCH_2CH_2NH_2$, $CH_2=CHCH_2NH_2$,

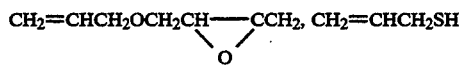
$CH_2=CHCH_2OCH_2CH\underset{O}{\overset{}{\diagdown\diagup}}CCH_2$, $CH_2=CHCH_2SH$

$CH_2=CHSi\{O(CH_2)_2OCH_3\}_3$, $CH_2=CHCH_2N(HCl)HCH_2CH_2NHCH_2(C_6H_4)CH=CH_2$, and other similar such compounds.

The unsaturated organic compound can be a silicon compound comprising substituted and unsubstituted organic substituents as described by, for example, formulas $(CH_2=CH(CH_2)_c)_dR^1{}_eSi(OR^1)_{4-d-e}$ and  $(CH_2=CH(CH_2)_c)_dR^1{}_eSiCl_{4-d-e'}$ where $R^1$ is as previously described, $C=0$ to 12, $d=1$ to 3, $e=0$ to 2, and $e+d=1$ to 3.

Prior to contact of the silicon hydride with the unsaturated reactant, it may be preferable to treat or purify the unsaturated reactant. Methods useful for treating or purifying the unsaturated reactants are those known in the art for treating or purifying unsaturated organic compounds and include but are not limited to distillation and treatment with an adsorbent such as alumina or molecular sieves.

The relative amounts of silicon hydride and unsaturated reactant used in the present process can be varied within wide limits. Although one unsaturated carbon-carbon linkage per silicon bonded hydrogen atom is stoichiometric there is no requirement that the process be run under stoichiometric conditions. Generally, it is preferred that the process be run with a stoichiometric excess of silicon hydride. Preferred is when the process is run with about 0.1 to ten percent stoichiometric excess of silicon hydride.

The silicon hydride and unsaturated reactant are contacted in the presence of a catalyst selected from a group consisting of platinum compounds and platinum complexes. Any platinum containing material which effects the reaction between the silicon hydride and an unsaturated carbon-carbon bond of the unsaturated organic compound is useful in the present invention. Examples of platinum catalysts useful in the present process are described, for example, in Onopchenko, U.S. Pat. No. 4,578,497; Lamoreaux, U.S. Pat. No. 3,220,972; and Speier, U.S. Pat. No. 2,823,218 all of which are hereby incorporated herein by reference.

The catalyst can be, for example, chloroplatinic acid, chloroplatinic acid hexahydrate, Karstedt's catalyst (i.e. a complex of chloroplatinic acid with sym-divinyltetramethyldisiloxane), dichlorobis(triphenylphosphine)platinum(II), cis-dichlorobis(acetonitrile)platinum(II), dicarbonyldichloroplatinum(II), platinum chloride, and platinum oxide.

A preferred platinum catalyst is selected from the group consisting of chloroplatinic acid, chloroplatinic acid hexahydrate, and platinum vinylsiloxane complexes such as a neutralized complex of chloroplatinic acid with sym-divinyltetramethyldisiloxane.

Generally, those concentrations of catalyst which provide about one mole of platinum per billion moles of unsaturated carbon-carbon bonds added to the process by the unsaturated reactant may be useful in the present process. Concentrations of catalyst providing as high as about one mole of platinum per one thousand moles of unsaturated carbon-carbon bonds added to the process by the unsaturated reactant may be useful. Higher concentrations of platinum may be used if desired. A preferred concentration of platinum catalyst is that providing about one to 1000 moles of platinum per $1\times10^6$ moles of unsaturated carbon-carbon bonds provided to the process by the unsaturated reactant.

The catalyst may be dissolved in a solvent for ease of handling and to facilitate measuring the small amounts typically needed. Suitable solvents include, for example, non-polar hydrocarbon solvents such as benzene, toluene, and xylene and polar solvents such as alcohols, glycols, and esters.

The present process is carried out in the presence of an unsaturated ketone accelerator described above by formulas (2) and (3), where $R^2$ is selected from a group consisting of alkyls comprising one to 12 carbon atoms, each $R^3$ is independently selected from a group consisting of hydrogen and alkyls comprising one to four carbon atoms, $R^4$ is selected from a group consisting of hydrogen and non-aryl monovalent hydrocarbon radicals comprising about one to 12 carbon atoms, n is a value within a range of zero to four, and m is a value within a range of about one to 17. Preferred is where m=3.

The substituent $R^2$ can be, for example, methyl, ethyl, propyl, isopropyl, butyl, and tertiary butyl. Preferred is when $R^2$ is selected from a group consisting of methyl and ethyl. The substituent $R^3$ can be hydrogen or an alkyl comprising one to four carbon atoms as described for $R^2$. Preferred is when $R^3$ is selected from a group consisting of hydrogen and methyl. Substituent $R^4$ can be hydrogen or any non-aryl monovalent hydrocarbon radical comprising one to about 12 carbon atoms. $R^4$ can be, for example, an alkyl radical such as methyl, ethyl, propyl, isopropyl, butyl, tertiary butyl, pentyl, and hexyl; a cycloalkyl such as cyclopentyl and cyclohexyl; an alkenyl radical such as vinyl, allyl, and pentenyl; substituted cycloalkenyls such as

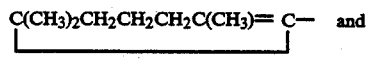

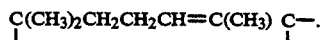

Preferred is when $R^4$ is selected from a group consisting of hydrogen, methyl

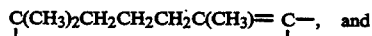

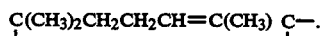

The unsaturated ketone accelerator can be, for example, α-ionone, β-ionone, 4-hexene-3-one, ethylvinylketone, 2-cyclohexene-1-one, isophorone, mesityl oxide, and 5-hexene-2-one. A preferred unsaturated ketone accelerator is selected from a group consisting of α-ionone, β-ionone, 4-hexene-3-one, ethylvinylketone, 2-cyclohexene-1-one, and isophorone.

An effective concentration of the unsaturated ketone accelerator is added to the present process, where an effective concentration is one that facilitates initiation of the reaction between the silicon hydride and the unsaturated organic compound, accelerates the rate of the reaction, or reduces loss of reactivity of the catalyst in the process. A useful effective concentration of the accelerator is generally within a rankle of about 0.01 to 20 weight percent of the weight of the unsaturated reactant. Preferred is when the accelerator is about 0.1 to ten weight percent of the weight of the unsaturated reactant.

The presence of oxygen during conduct of the present process can enhance reaction parameters such as the reaction rate and selectivity of addition when the solution concentration of oxygen is controlled relative to platinum catalyst in the reaction mixture. The oxygen can be added into the reaction mixture by bubbling it into one of the reactants or by bubbling it into the reaction mixture. Contacting the oxygen on the surface of the liquid, such as by blowing oxygen into the vapor space of the reactor or by purging the reactor system with oxygen may also be used, but may not be as effective due to mass transfer considerations.

The effective amount of oxygen to be added to the present process will be dependent upon such factors as the operating conditions, the reactants, and the amount of catalyst present. It is preferred to introduce the oxygen into the process combined with an inert gas at an oxygen level of parts per million to about 20 weight percent, based on the combined weights of the oxygen and inert gas. More preferred is when the oxygen is diluted in an inert gas to about 0.1 to 40 weight percent. The inert gas can be, for example, nitrogen or argon. Typically, the preferred amount of oxygen to be added to the process can be determined by monitoring the rate of reaction and by-product formation. A process for adding oxygen to a hydrosilation process is described, for example, in co-pending U.S. patent application 08/099,783, filed Jul. 30, 1993, which is hereby incorporated herein by reference as a further description of the way oxygen may be used in the present process.

The following examples are provided to illustrate the present invention. These examples are not intended to limit the claims herein.

EXAMPLE 1

A variety of unsaturated ketones were evaluated for their ability to accelerate the reaction of methyldichlorosilane with cyclohexene in the presence of a platinum catalyst.

A stock mixture was prepared in an argon purged and blanketed bottle. The stock mixture comprised four molar percent excess of methyldichlorosilane in cyclohexane which had been treated with 13X molecular sieves. About $6 \times 10^{-5}$ moles of platinum, as a complex prepared by the reaction of chloroplatinic acid with sym-divinyltetramethyldisiloxane, per mole of cyclohexene was added to the stock mixture. Aliquots of this catalyzed stock solution were then transferred to argon-purged glass tubes and unsaturated ketones as listed in Table 1 were added to individual tubes at a concentration of 1 weight percent of the cyclohexene present in the tube. The tubes were then heat sealed under argon purge and heated at 80° C. for three hours. At the end of three hours the tubes were cooled and the contents analyzed by gas chromatography using a thermal conductivity detector (GC-TC). The results of this analysis are reported in Table 1 as the average area percent of methyl(cyclohexyl)dichlorosilane (MeC$_H$SiCl$_2$) under the GC-TC trace for the number of replicate samples provided in parentheses.

TABLE 1

Effect of Unsaturated Ketones on Reaction of Methyldichlorosilane with Cyclohexene

| Unsaturated Ketone | Area % MeC$_H$SiCl$_2$ |
| --- | --- |
| None | 33.9 (n = 7) |
| 2-Cyclohexene-1-one | 82.5 (n = 1) |
| α-Ionone | 79.5 (n = 3) |

TABLE 1-continued

Effect of Unsaturated Ketones on Reaction of
Methyldichlorosilane with Cyclohexene

| Unsaturated Ketone | Area % MeC$_H$SiCl$_2$ |
|---|---|
| β-Ionone | 79.9 (n = 3) |
| 4-Hexene-3-one | 77.0 (n = 3) |
| Isophorone | 85.3 (n = 1) |
| Mesityl oxide | 70.1 (n = 2) |
| Ethylvinylketone | 67.4 (n = 3) |
| Trans-4-phenyl-3-butene-2-one* | 32.8 (n = 2) |
| 2-Methyl-2-cyclopentene-1-one* | 8.5 (n = 2) |

*Not within scope of present invention.

EXAMPLE 2

The effect of oxygen on the unsaturated ketone acceleration of the reaction of methyldichlorosilane with cyclohexene in the present of a platinum catalyst was evaluated.

A comparison run was made to evaluate the effects of oxygen in the absence of an unsaturated ketone accelerator. A dried flask was purged with a 2% O$_2$/N$_2$ purge and then charged with 0.95 mole of cyclohexene which had been treated with 13X molecular sieves. About $1.2 \times 10^{-4}$ moles of platinum, as a complex prepared by the reaction of chloroplatinic acid with sym-divinyltetramethyldisiloxane, per mole of cyclohexene was added to the flask. This mixture was then heated to about 80° C. and about 0.91 moles of methyldichlorosilane added to the flask at a rate of 1.8 mL/min.

A sample was taken from the flask at 174 minutes and analyzed by GC-TC. The amount of methyl(cyclohexyl)dichlorosilane produced is reported in Table 2 as the area percent under the GC-TC trace.

A second run was made, as described for the comparison run, in the presence of 1 weight percent 2-cyclohexene-1-one, based on weight of cyclohexene. The amount of methyl(cyclohexyl)dichlorosilane produced in the presence of both oxygen and unsaturated ketone accelerator is reported in Table 2 as the area percent under the GC-TC trace.

TABLE 2

Effects of Oxygen and 2-Cyclohexene-1-one on Reaction of
Methyldichlorosilane With Cyclohexene

| Unsaturated Ketone | 2% O$_2$/N$_2$ | Time (Min.) | Area % MeC$_H$SiCl$_2$ |
|---|---|---|---|
| None | Yes | 174 | 59.6 |
| 2-Cyclohexene-1-one | Yes | 130 | 93.6 |

EXAMPLE 3

The ability of α-ionone to accelerate the reaction of methyldichlorosilane with cyclopentene in the presence of a platinum catalyst was evaluated. A platinum catalyzed stock mixture as described in Example 1 was prepared replacing the cyclohexene with cyclopentene. The mixture was reacted by the method as described in Example 1 for three hours at 80° C. in the presence of 1 weight percent α-ionone, based on the weight of cyclopentene. A comparison run was made without the addition of α-ionone. The results are reported in Table 3 as the area percent of methyl(cyclopentyl)dichlorosilane (MeC$_p$SiCl$_2$) under the GC-TC trace.

TABLE 3

Effect of Alpha-Ionone on Reaction of
Methylchlorosilane With Cyclopentene

| unsaturated ketone | Area % MeC$_p$SiCl$_2$ |
|---|---|
| None | 85.6 |
| α-Ionone | 85.0 |

Although not evidenced by the data in Table 3, the inventors believe the rate of reaction to be faster when α-ionone is used as an accelerator in the described reaction.

EXAMPLE 4

The effect of β-ionone on the platinum catalyzed reaction of dichlorosilane with cyclopentene was evaluated. The reaction was conducted in argon-purged sealed tubes as described in Example 1. The sealed tubes contained a mixture comprising a molar ration of dichlorosilane (H$_2$SiCl$_2$) to cyclopentene of 0.096 to 1.0. About $1 \times 10^{-4}$ moles of platinum complexed as described in Example 1 was added per mole of dichlorosilane. The mixture was tested in the presence and absence of 1 volume percent β-ionone, based on total volume, for the times and temperatures described in Table 4. The contents of the tubes were cooled at the end of the reaction periods and analyzed by GC-TC. The results are presented in Table 4 as the area percent under the GC-TC trace for cyclopentyldichlorosilane (C$_p$HSiCl$_2$) and cyclopentyltrichlorosilane (C$_p$SiCl$_3$).

TABLE 4

Effect of β-Ionone on Reaction of Dichlorosilane
With Cyclopentene

| Unsaturated Ketone | Time (Min.) | Temp. (°C.) | Area % C$_p$HSiCl$_2$ | Area % C$_p$SiCl$_3$ |
|---|---|---|---|---|
| None | 90 | 120 | 11.2 | 0.0 |
| β-Ionone | 30 | 24 | 10.4 | 0.6 |
| β-Ionone | 60 | 120 | 11.8 | 0.6 |

We claim:
1. A hydrosilation process comprising: contacting
(A) a silicon hydride described by formula

$$R^1{}_aH_bSiCl_{4-a-b},$$

where each $R^1$ is independently selected from a group consisting of alkyls comprising one to 12 carbon atoms, cycloalkyls comprising four to 12 carbon atoms, and aryls; a=0 to 3, b=1 to 3, and a+b=1 to 4; and (B) an unsaturated reactant selected from a group consisting of
(i) substituted and unsubstituted unsaturated organic compounds or mixtures thereof
(ii) silicon compounds comprising substituted or unsubstituted unsaturated substituents, and
(iii) mixtures of (i) and (ii);

in the presence of a catalyst selected from a group consisting of platinum compounds and platinum complexes and an accelerator selected from a group consisting of unsaturated ketones described by formulas

and

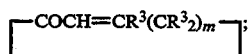

where $R^2$ is selected from a group consisting of alkyls comprising one to 12 carbon atoms, each $R^3$ is independently selected from a group consisting of hydrogen and alkyls comprising one to four carbon atoms, $R^4$ is selected from a group consisting of hydrogen and non-aryl monovalent hydrocarbon radicals comprising about one to 12 carbon atoms, $n=0$ to 4, and $m=1$ to 17.

2. A process according to claim 1, where each $R^1$ is independently selected from a group consisting of alkyls comprising one to about six carbon atoms.

3. A process according to claim 1, where $R^1$ is methyl.

4. A process according to claim 1, where the silicon hydride is selected from a group consisting of methyldichlorosilane and dichlorosilane.

5. A process according to claim 1, where the unsaturated reactant is selected from a group consisting of cyclohexene and cyclopentene.

6. A process according to claim 1, where the unsaturated reactant is cyclohexene.

7. A process according to claim 1, where the process is run with about 0.1 to ten percent stoichiometric excess of silicon hydride.

8. A process according to claim 1, where the platinum catalyst is selected from a group consisting of chloroplatinic acid, chloroplatinic acid hexahydrate, and a platinum vinylsiloxane complex.

9. A process according to claim 1, where the platinum catalyst is a platinum vinylsiloxane complex.

10. A process according to claim 8, where the concentration of platinum catalyst is that providing about one to 1000 moles of platinum per $1 \times 10^6$ moles of unsaturated carbon-carbon bonds provided to the process by the unsaturated reactant.

11. A process according to claim 1, where $R^2$ is selected from a group consisting of hydrogen and methyl, $R^3$ is selected from a group consisting of hydrogen and methyl, and $R^4$ is selected from group consisting of hydrogen, methyl,

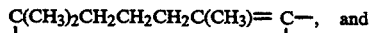, and

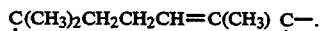.

12. A process according to claim 1, where $R^3$ is selected from a group consisting of hydrogen and methyl and $m=3$.

13. A process according to claim 1, where the unsaturated ketone is selected from a group consisting of α-ionone, β-ionone, 4-hexene-3-one, ethylvinylketone, 2-cyclohexene-1-one, and isophorone.

14. A process according to claim 1, where the concentration of the unsaturated ketone is about 0.01 to 20 weight percent of the weight of the unsaturated organic compound.

15. A process according to claim 1, where the concentration of the unsaturated ketone is about 0.1 to 10 weight percent of the unsaturated organic compound.

16. A process according to claim 1, further comprising the=presence of oxygen during contact of the silicon hydride and unsaturated reactant.

17. A process according to claim 16, where the oxygen is introduced into the process combined with an inert gas at an oxygen level of about 0.1 to 40 weight percent of the combined weights of the oxygen and the inert gas.

18. A process according to claim 1, where the silicon hydride is selected from a group consisting of methyldichlorosilane and dichlorosilane, the unsaturated organic compound is cyclohexene, the platinum catalyst is a platinum vinylsiloxane complex and the unsaturated ketone is selected from a group consisting of α-ionone, β-ionone, 4-hexene-3-one, ethylvinylketone, 2-cyclohexene-1-one, mesityloxide and isophorone.

* * * * *